United States Patent
Greiser

(10) Patent No.: US 10,957,443 B2
(45) Date of Patent: Mar. 23, 2021

(54) MEDICAL IMAGING APPARATUS AND METHOD FOR PROVIDING A RANGE OF PARAMETERS FOR OPERATION THEREOF

(71) Applicant: Siemens Healthcare GmbH, Erlangen (DE)

(72) Inventor: Andreas Greiser, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 53 days.

(21) Appl. No.: 16/260,821

(22) Filed: Jan. 29, 2019

(65) Prior Publication Data

US 2019/0237185 A1 Aug. 1, 2019

(30) Foreign Application Priority Data

Jan. 30, 2018 (EP) .................................... 18154137

(51) Int. Cl.
| | |
|---|---|
| *G16H 30/40* | (2018.01) |
| *G16H 30/20* | (2018.01) |
| *G16H 40/63* | (2018.01) |
| *A61B 6/00* | (2006.01) |
| *A61B 5/055* | (2006.01) |
| *G06T 7/00* | (2017.01) |

(52) U.S. Cl.
CPC .............. *G16H 30/40* (2018.01); *G16H 30/20* (2018.01); *G16H 40/63* (2018.01); *A61B 5/055* (2013.01); *A61B 6/481* (2013.01); *G06T 7/0012* (2013.01)

(58) Field of Classification Search
None
See application file for complete search history.

(56) References Cited

U.S. PATENT DOCUMENTS

| | | | |
|---|---|---|---|
| 2007/0276221 A1 | 11/2007 | Warntjes | |
| 2008/0242973 A1* | 10/2008 | Warmuth | G01R 33/5602 600/413 |
| 2009/0290778 A1* | 11/2009 | Sun | G06T 7/149 382/131 |
| 2013/0267842 A1* | 10/2013 | Scheuering | A61B 6/563 600/431 |

OTHER PUBLICATIONS

Bernstein et al., "Handbook of MRI Pulse Sequences," Elsevier Science & Technology, Chapter 3.2, pp. 77-84 and Chapter 12, pp. 443-454 (2004).
European Action dated Jan. 20, 2021, Application No. 18 154 137.6.

* cited by examiner

*Primary Examiner* — Leon Viet Q Nguyen
(74) *Attorney, Agent, or Firm* — Schiff Hardin LLP

(57) ABSTRACT

In a method and medical imaging apparatus for providing a range of potential parameters that can be used for recording a future medical image data set, an algorithm is provided to a computer for performing a quantitative analysis of the future medical image data set. The computer is also provided with patient information specifying a status of a patient. In order to reduce a probability of an invalid quantitative analysis, the range of potential parameters is set in the computer by performing the quantitative analysis depending on the patient information.

10 Claims, 2 Drawing Sheets

MEDICAL IMAGING APPARATUS AND METHOD FOR PROVIDING A RANGE OF PARAMETERS FOR OPERATION THEREOF

BACKGROUND OF THE INVENTION

Field of the Invention

The present invention concerns a method for providing a range of potential parameters that can be used for recording a medical image data set, as well as a corresponding medical imaging apparatus, and a non-transitory, computer-readable data storage medium.

Description of the Prior Art

Recording medical image data sets, for example by operating a magnetic resonance tomography scanner, is well known. Typically, the recorded medical image data sets are reconstructed for visualization thereof on a screen in order to observe an inner structure of an organ or a part of an organ. In some cases, it is even possible to further specify sub-parts of the visualized parts of an organ, preferably for evaluating a particular tissue. For this purpose, besides the reconstruction, a quantitative analysis of the medical image data set is performed. Such a quantitative analysis preferably results in a set of key values, each of which further specifies a defined region in the visualization of the medical image data set. In turn, these key values are usually visualized, preferably in a presentation that merges information of the reconstructed medical image data set and the corresponding set of key values.

However, the quality of the key values strongly depends on the validity of the quantitative analysis. Therefore, sets of key values having a comparably high bias or offset are usually discarded. Consequently, recording of the medical image data set has to be repeated in order to obtain the desired set of key values that supports an interpretation of the visualized medical image data set. This disadvantageously extends the time for examining the patient.

SUMMARY OF THE INVENTION

In view of the above, it is an object of the present invention to provide an improved method for analyzing medical image data sets quantitatively, in particular in a time-efficient and effective way.

The above object is achieved according to the present invention by a method for providing a range of potential parameters that can be used for operating a medical imaging apparatus in order to acquire a medical image data set, wherein an algorithm is provided to a computer that, when executed by the computer, performs a quantitative analysis of the medical image data set that is to be acquired. The computer is also provided with patient information that specify a status of the patient from whom the medical image data set is to be acquired. The patient is used in the computer in the execution of the quantitative analysis algorithm so as to reduce the probability of an invalid quantitative analysis resulting from the execution of the algorithm.

Contrary to the state of the art according to the present invention, a range of potential parameters is set that can be used for recording the medical image data set in order to reduce the probability of an invalid quantitative analysis, i.e., an analysis resulting in inappropriate values that does not support the interpretation of the medical image data set. For example, the quantitative analysis is considered to be invalid when a bias exceeds a specific value. In particular, by considering the status of the patient, it is advantageously possible to increase the probability that the quality of the recorded medical image data set allows a valid quantitative analysis. As a consequence, recording a new medical image data set can be avoided, advantageously. Simultaneously, the method allows providing a range of potential parameters and thus the user can adapt the parameter for recording more flexibly and is not restricted to one set of parameters that guarantees a high quality. As a consequence, the time for recording the medical image data set can be optimized without reducing the needed quality of the recorded medical image data set, for instance. Furthermore, the range of the potential parameters depends on the algorithm chosen for the quantitative analysis, i.e., the range of potential parameters depends on both the algorithm and the status of the patient. Consequently, the range of potential parameters is advantageously adapted to the respective algorithm and its requirements for the recorded medical image data set. Preferably, the algorithm includes execution of an inline fit routine.

In general, the medical image data set is recorded by a medical imaging device or a scanner, such as a magnetic resonance tomography (MRT) scanner or a computed tomography scanner. For visualization, the medical image data set is reconstructed and the quantitative analysis is performed in addition to the reconstruction. A processor is configured to perform the quantitative analysis. The processor may be a part of a network or is part of a workstation of the scanner. Preferably, the processor is configured for performing the reconstruction and/or the quantitative analysis. In particular, the results of the reconstruction and/or the quantitative analysis are visualized, preferably in a merged form, on a screen or display, such as on a screen or display of a workstation, smartphone and/or tablet. A workstation might be a (personal) computer, a virtual running machine on host hardware, a microcontroller, or an integrated circuit. As an alternative, the workstation can be a real or a virtual group of computers. Preferably, the workstation has a calculation unit and a memory. The calculation unit involve hardware elements and software elements, for example a microprocessor or a field programmable gate array. The memory can be embodied as non-permanent main memory (e.g. random access memory) or a permanent mass storage (e.g. a hard disk, USB stick, SD card, solid state disk). Preferably, the workstation is a part of the medical imaging apparatus. It is also thinkable that at least one of the steps of the method is performed on a server or at the cloud.

Preferably, the parameter of the range of potential parameters defines a setting of the device for recording the medical image data set. For example, the parameter defines a duration of a scan, a frequency of measuring, a trigger for measuring or the like. Thereby, it is conceivable that the range of potential parameters forms an interval or the potential parameters are discrete values. A user can set the parameter via an input device, such as a human machine interface like a keyboard. Thus the range of potential parameters is provided, in particular visualized, to the user and the user can choose the parameter being preferred to him, for example by inserting a parameter value via the human machine interface or choose the parameter from a list. It is also possible for the user to select between different algorithms for identifying the algorithm that allows using the parameter being preferred by the user.

According to a preferred embodiment of the present invention, the set of potential parameters is provided before recording the future medical image data set. That means the requirements for a valid analysis are already checked before the medical image data set is recorded and not after recording the medical image data set as it is usually done in the state of the art by considering the recorded medical image data set. As a consequence, recording a medical imaging data set that cannot be analyzed appropriately can be avoided, advantageously.

In a further embodiment of the present invention, it is provided that a set of key values is provided as a result of the quantitative analysis, wherein the key values are preferably visualized on a screen. The key values allow a further specification of a defined region of the visualized medical imaging data set and therefore presents an additional information to the user. Preferably, the respective key value can be assigned to a specific region of the medical image data set and for a visualization the information of the reconstructed medical image data set and the key values are merged.

Preferably, a current status of the patient is specified by the patient information. For example, a cardiac cycle or a pulse frequency represents information that specify the current status of the patient. As a consequence, the range of potential parameters can adapted to the current status of the patient. Further, it is possible that by appropriately choosing the parameter, in particular a trigger parameter, the recording of the medical image data set is synchronized with the current status of the patient for increasing the probability of a medical image data set that can be validly analyzed. The current status can be recorded or measured directly before or during providing the range of potential parameters.

Alternatively or in addition, a general status of the patient is specified by the patient information. For example, information regarding the general status of a patient comprises tissue information, and the range of the potential parameters is set based on this general information. The general information might be included in a set of patient-related information. For example, the general information is included in a PACS file and is extracted from this PACS file automatically for being considered to set the range of potential parameters.

In a preferred embodiment, warning information is provided to a user, when a selected parameter out of the range of the potential parameters is chosen. By providing the warning information in humanly perceptible form, the user can be informed visually or audibly about the risk of recording a medical image data set that cannot be analyzed appropriately. Subsequently, the user can decide, whether he or she wants to switch the algorithm, switch the parameter or record the medical image data set and analyze the recorded medical image data set by using a further algorithm.

Preferably, a control value is provided, wherein the control value depends on the patient information and/or the selected parameter, wherein the control value is compared to a threshold value. By using the control value it is possible to decide on a case-by-case basis, whether the selected parameter matches with the range of potential parameters. The threshold value may be adjustable, for example by the user via the human machine interface. Thus, it is possible to individually adapt the requirements for the quality of the medical image data sets.

The control value and/or the threshold value can be defined by using artificial neural network. Thus, the condition for setting the range of potential parameters can be provided on basis of the experience of the artificial neural network and the range of potential parameters might be expanded. Thereby the artificial neural network preferably considers the algorithm for setting the respective control value and/or threshold value. Thereby the artificial neural network can be shared by several different scanners for recording medical image data sets.

According to another embodiment of the present invention, the medical image data set is recorded by using a selected parameter out of the range of potential parameters, and is preferably saved for a subsequent analysis performed by a further algorithm. In other words, it allows the user to perform the recording of the medical image data set although the selected parameter is out of the range of potential parameters. Thus, the user has the possibility to perform a subsequent analysis by the further algorithm that might result in a valid analysis since the further algorithm can handle the specifics caused by the selected parameter in a more appropriate way.

In a preferred embodiment of the present invention, the medical image data set is recorded and the quantitative analysis is performed automatically, in particular exclusively automatically, when the selected parameter corresponds to a value in the range of the potential parameters. Thus, there is no need for a further interaction by the user advantageously, when a proper parameter is selected.

Preferably, the medical image data set is recorded by a magnetic resonance tomography scan, wherein the selected parameter defines the time between two inversion pulses of the magnetic resonance tomography scan, wherein the patient information comprises information about the cardiac cycle of the patient. Preferably, the key value is represented by the T1-values. Thus, the duration between two inversion parameters can be adapted to the cardiac cycle for increasing the probability for recording a medical image data set that can be analyzed appropriately and provides proper T1-values.

The present invention also encompasses a medical imaging apparatus having a computer that is designed to implement the method according to the invention, as described above, and to then use the parameters determined by the execution of the quantitative analysis algorithm, embodying the patient information, to then operate the medical imaging apparatus so as to acquire the medical image data set from the patient.

The present invention also encompasses a non-transitory, computer-readable data storage medium encoded with programming instructions that, when the storage medium is loaded into a computer, cause the computer to implement any or all embodiments of the method according to the invention, as described above.

DESCRIPTION OF THE PREFERRED EMBODIMENTS

Figure 1:
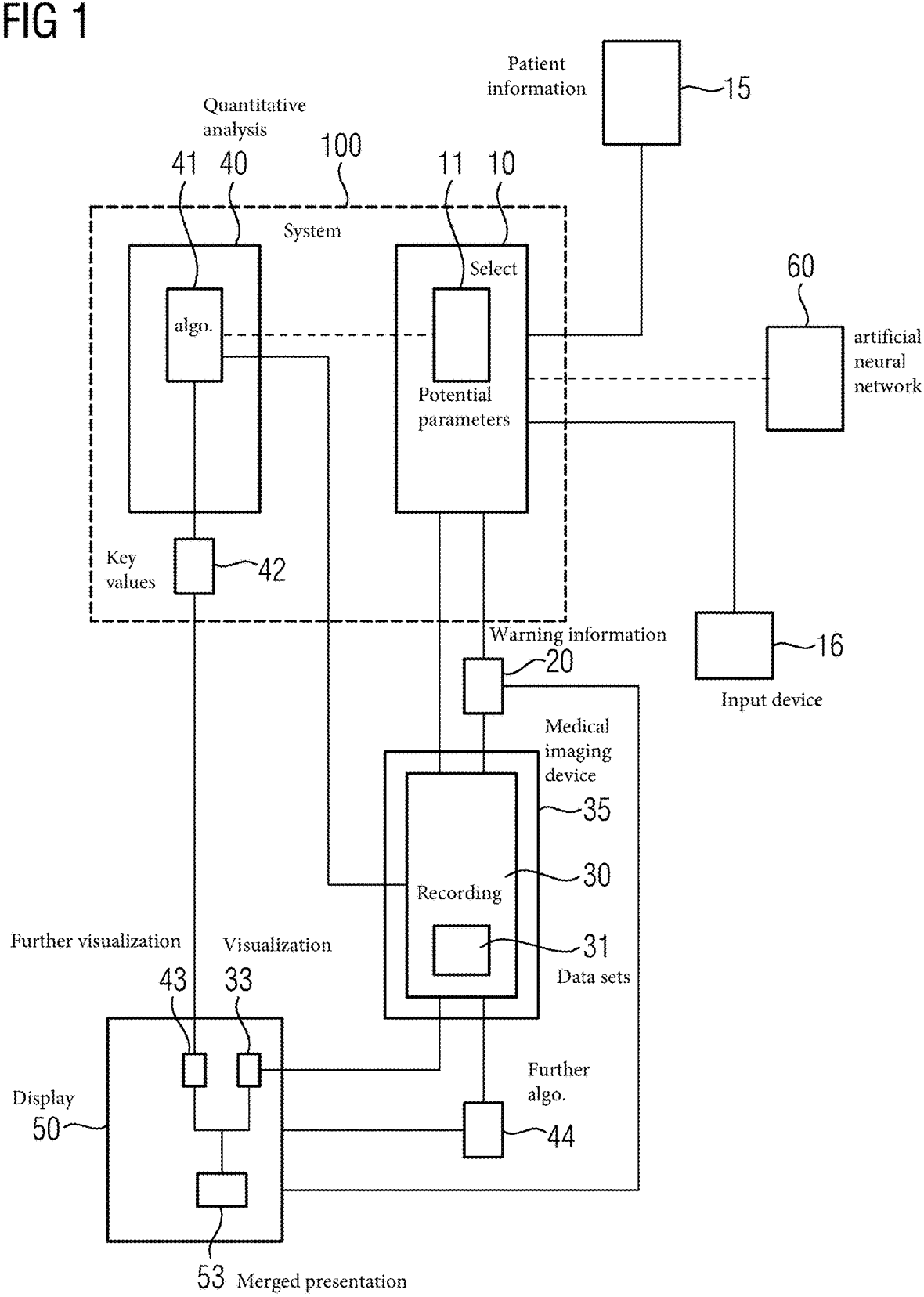
FIG. 1 schematically illustrates the method according to a preferred embodiment of the present invention.

In FIG. 1, a block diagram is presented that schematically illustrates the method for providing a range of potential parameters 11 that can be used for recording a future medical image data set 31 according to a preferred embodiment of the present invention. For instance, such a medical image data set 31 is provided by recording 30 a magnetic resonance tomography (MRT) scan by means of a medical imaging device 35. Besides visualizing the medical image data sets 31 to show the shape or inner structure of an organ, in particular of parts of the organ, it is preferably provided that further specifications of the medical image data set 31 are specified by key values 42. Preferably, these key values 42 are mapped or assigned to specific regions of the visualized medical image data set and for example help to differentiate different kinds of tissues. Thereby it is thinkable that a visualization 33 of the medical image data set 31 and a further visualization 43 representing the key values are merged in a merged presentation 53 and presented to a user on a screen 50.

Such key values 42 are a result of a quantitative analysis 40 of the medical image data set 31, in particular by using an algorithm 41 such as a fitting routine. However, for providing valid key values 42, the recorded medical image data sets 31 have to satisfy specific quality criteria. Otherwise, the key values 42 provided by the quantitative analysis 40 cannot support the user, for example due to a comparable high bias of the provided key values 42. For reducing the probability of performing an invalid analysis that results in a non-useable set of key values 42, the possibility for choosing 10 a parameter from a range of potential parameters 11 is provided, wherein the range of potential parameters 11 is chosen such that a probability of an invalid quantitative analysis is reduced by a parameter chosen from the set range of parameters 11. As a consequence, the user can choose, preferably via an input device 16, the parameter for a planned future medical image data set such that the algorithm 41 very likely provides a valid set of key values 42. Therefore, the amount of analyzes resulting in invalid results and consequently the time needed for effectively recording and analyzing medical image data sets 31 is reduced. In particular, recording a further medical image data set 31 can be avoided in such cases in that the quantitative analysis 40 gives evidence that the recorded medical image data set 31 cannot be used and there is a need for recording a new medical image data set 31.

For example, the key values 42 are represented as T1-values of a MRT-scan and the parameter 11 for recording a future medical image data set 31 is preferably a sampling rate. Preferably, the sampling rate is chosen such that the duration of the MRT-scan is reduced. However, for providing the T1-value having an appropriate accuracy the sampling rate has to be chosen such that the time between two inversion pulses should be five times bigger than the T1-value. For example, the time between should be about 5 seconds.

Figure 2:
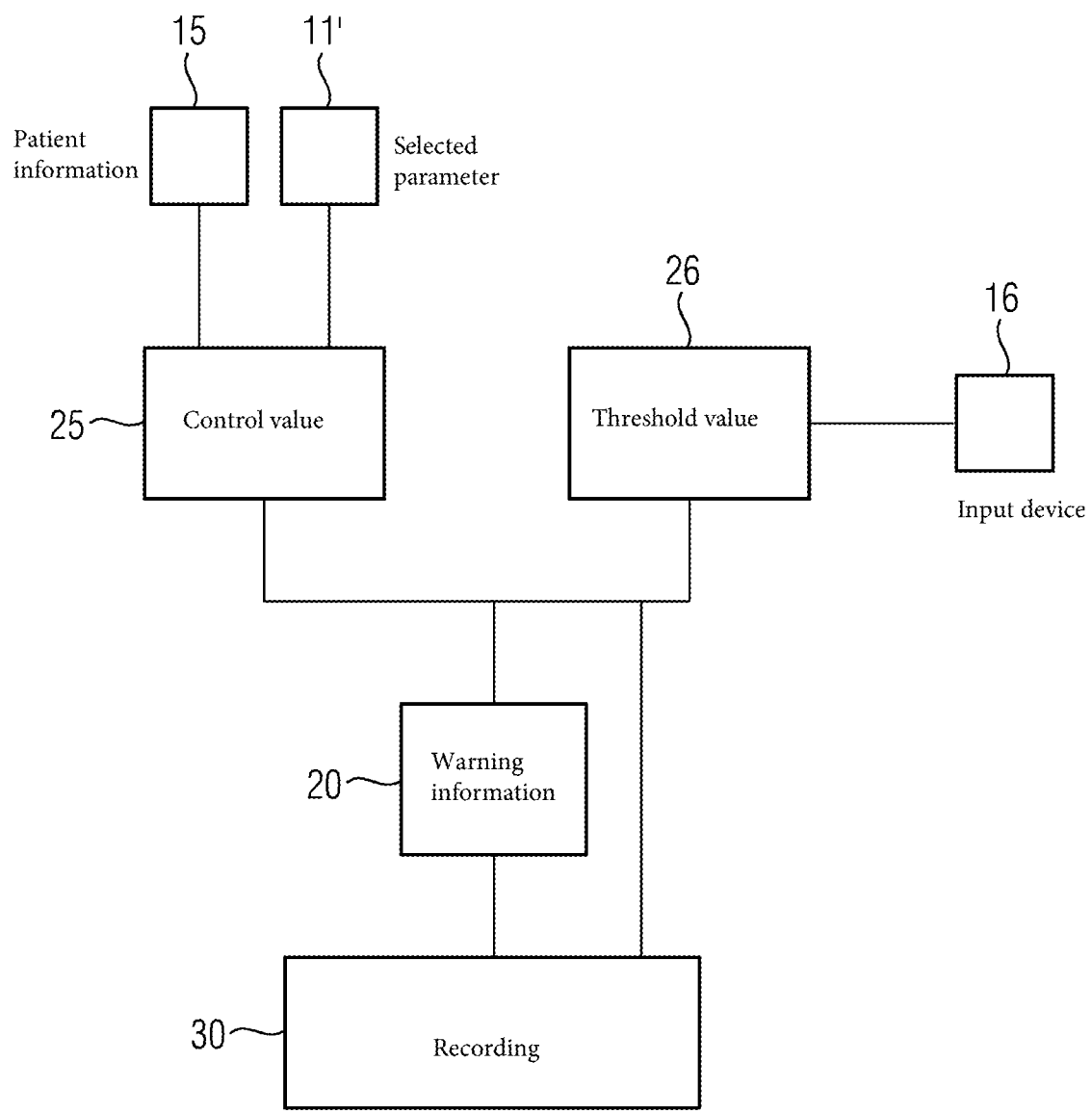
FIG. 2 schematically illustrates a detail of the method according to the preferred embodiment of the present invention.

Furthermore, the range of potential parameters 11 for recording the future medical image data set 31 is based on a status of a patient. In particular, patient information 15 specifying the status of the patient is provided and subsequently the range of potential parameters 11 is set depending on the patient information 15. For example, for providing the range of potential parameters 11, the status of the patient is considered for reducing the probability of an invalid quantitative analysis 40. In particular, —as illustrated in FIG. 2 in detail—a control value 25 based on the patient information 15 and/or on a selected parameter 11' for recording the future medical image data set 31 is provided and compared to a threshold value 26, preferably to an adjustable threshold value 26. When the control value 25 for example exceeds the threshold value 26, a quantitative analysis 40 is performed, in particular automatically, whereas a warning information 20 is provided to the user, when the control value 25 is smaller than the threshold value 26. Preferably, the user can choose whether he or she wants to modify the selected parameters 11' or to continue recording the medical image data set 31 for analyzing the recorded medical image data set by a further algorithm 44, wherein the further algorithm 44 preferably differs from the algorithm 41 used in general.

For example, the duration between two inversion pulses corresponds to 5 times T1 and the duration is measured in units of heart beats of the patient (#HB). The control value 25 might be represented by the product of the duration (#HB) between two inversion pulses and a cardiac cycle (RR) and the threshold value 26 is presented by 5 times T1m, wherein T1m is adjustable by the user for example. For instance, a system 100 for performing the method is configured by the following control string:

```
If (#HBs × RR > 5 × T1m) && !(IS_POST_CONTRAST_SCAN)
{
Perform inline fit
}
Otherwise
{
Throw warning:
"Data not valid for inline fit! → Change parameters or apply suitable
   offline fit"
}
```

For a T1m value having a duration of 1 s and a cardiac cycle of 0.9 s, the algorithm 41 is performed, when the duration between two inversion pulses exceeds six heartbeats and a warning information 20 is presented to the user, in particular on the screen 50, when the duration between two inversion pulses is equal or smaller than five heartbeats.

Furthermore, the system 100 can be in communication with, or include, an artificial neural network 60. This artificial neural network 6 preferably sets a definition for the threshold value 26 and/or the control value 25. Thus, it is possible to use the previous experience of the artificial neural network 60 to provide a proper condition that increases the probability of a valid analysis of the medical image data set 31.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for providing a range of parameters available for use for operating a medical imaging apparatus in order to acquire a set of medical image data, said method comprising:

providing a processor with an algorithm that performs a quantitative analysis of said medical image data set;

providing said processor with information that specifies a status of a patient from whom the medical image data set is to be acquired;

executing said algorithm by using said patient information to reduce a probability of an invalid quantitative analysis of said medical image data set, in order to produce a quantitative analysis result from said algorithm;

in said processor, using said quantitative analysis result to determine a range of parameters for use in operating said medical imaging apparatus to acquire said medical image data set from said patient, and making a presentation of said range of parameters available in electronic form as an output from said processor;

after presenting said range of parameters, allowing a user to enter a designation of a selected parameter into the processor;

in said processor, producing a control value from at least one of said patient information and said selected parameter, and comparing said control value to a threshold value to determine whether said selected parameter is outside of said range of parameters; and in said processor, generating a humanly-perceptible warning if said selected parameter is outside of said range of parameters.

2. A method as claimed in claim 1, comprising:
presenting said range of parameters in a visual format on a display screen in communication with said processor.

3. A method as claimed in claim 1, comprising:
including, in said patient information, a designation of a current status of the patient.

4. A method as claimed in claim 1, comprising:
including, in said patient information, a designation of a general status of the patient.

5. A method as claimed in claim 1, comprising:
in said processor, determining at least one of said control value and said threshold value using an artificial neural network.

6. A method as claimed in claim 1, comprising:
despite said selected parameter being outside of said range of parameters, operating said medical imaging apparatus to acquire said medical image data set from the patient using said selected parameter; and
storing the acquired medical image data set, which was acquired using said selected parameter that is outside of said range of parameters, for subsequent analysis by a further algorithm in said processor.

7. A method as claimed in claim 1, comprising:
when said selected parameter is determined to be within said range of parameters, automatically operating said medical imaging apparatus to acquire said medical image data set from the patient using the selected parameter.

8. A method as claimed in claim 1, wherein:
said medical imaging apparatus is a magnetic resonance tomography apparatus,
said medical image data set is acquired by operating said magnetic resonance tomography apparatus to perform a magnetic resonance tomography scan,
said selected parameter defines a time between two inversion pulses of the magnetic resonance tomography scan, and
said patient information describes a cardiac cycle of the patient.

9. A computer for providing a range of parameters available for use for operating a medical imaging apparatus in order to acquire a medical image data set, said computer comprising:
a memory storing an algorithm; and
a processor executing the algorithm to perform a quantitative analysis of said medical image data set;
said processor being further configured to:
obtain information that specifies a status of a patient from whom the medical image data set is to be acquired;
execute said algorithm by using said patient information to reduce a probability of an invalid quantitative analysis of said medical image data set, in order to produce a quantitative analysis result from said algorithm;
use said quantitative analysis result to determine a range of parameters for use in operating said medical imaging apparatus to acquire said medical image data set from said patient, and to make a presentation of said range of parameters available in electronic form as an output from said processor;
after presenting said range of parameters, allowing a user to enter a designation of a selected parameter into the processor;
produce a control value from at least one of said patient information and said selected parameter, and comparing said control value to a threshold value to determine whether said selected parameter is outside of said range of parameters; and
generate a humanly-perceptible warning if said selected parameter is outside of said range of parameters.

10. A non-transitory, computer-readable data storage medium encoded with programming instructions, said storage medium being loaded into a computer comprising a processor, and said programming instructions causing said processor to provide a range of parameters available for use for operating a medical imaging apparatus to acquire a medical image data set by:
receiving an algorithm that performs a quantitative analysis of said medical image data set;
receiving information that specifies a status of a patient from whom the medical image data set is to be acquired;
executing said algorithm by using said patient information to reduce a probability of an invalid quantitative analysis of said medical image data set, in order to produce a quantitative analysis result from said algorithm; and
using said quantitative analysis result to determine a range of parameters for use in operating said medical imaging apparatus to acquire said medical image data set from said patient, and make a presentation of said range of parameters available in electronic form as an output from said processor
after presenting said range of parameters, allowing a user to enter a designation of a selected parameter into the processor;
producing a control value from at least one of said patient information and said selected parameter, and comparing said control value to a threshold value to determine whether said selected parameter is outside of said range of parameters; and
generating a humanly-perceptible warning if said selected parameter is outside of said range of parameters.

* * * * *